(12) United States Patent
Winston et al.

(10) Patent No.: US 8,795,638 B1
(45) Date of Patent: Aug. 5, 2014

(54) COMPOSITIONS FOR DENTAL CARE

(75) Inventors: Anthony Errol Winston, East Brunswick, NJ (US); Richard F. Stockel, Bridgewater, NJ (US); Anthony Joseph Sawyer, Albuquerque, NM (US)

(73) Assignee: Nevada Naturals Inc., Albuquerque, NM (US)

( * ) Notice: Subject to any disclaimer, the term of this patent is extended or adjusted under 35 U.S.C. 154(b) by 0 days.

(21) Appl. No.: 13/200,997

(22) Filed: Oct. 6, 2011

Related U.S. Application Data

(63) Continuation-in-part of application No. 11/599,758, filed on Nov. 15, 2006, now abandoned, which is a continuation-in-part of application No. 10/647,752, filed on Aug. 26, 2003, now abandoned.

(51) Int. Cl.
*A61Q 11/00* (2006.01)
*A61K 8/00* (2006.01)
*A61K 8/18* (2006.01)

(52) U.S. Cl.
USPC ............. 424/49; 514/900; 514/901; 514/902; 424/54; 424/401; 433/215; 433/216; 433/217.1

(58) Field of Classification Search
USPC ........... 424/49, 54, 401; 433/215, 216, 217.1; 514/900, 901, 902
See application file for complete search history.

(56) References Cited

U.S. PATENT DOCUMENTS

| | | | |
|---|---|---|---|
| 3,825,560 A | 7/1979 | Saito et al. | |
| 4,997,851 A | 3/1991 | Isaacs et al. | |
| 5,434,182 A | 7/1995 | Isaacs et al. | |
| 5,780,658 A | 7/1998 | Martinez-Pardo et al. | |
| 5,874,068 A * | 2/1999 | Engelman et al. | 424/54 |
| 6,414,023 B1 | 7/2002 | Brandsborg et al. | |
| 6,447,758 B1 * | 9/2002 | Carale et al. | 424/54 |
| 6,509,022 B2 * | 1/2003 | Lowry et al. | 424/401 |
| 6,638,978 B1 | 10/2003 | Kabara | |
| 7,074,447 B2 | 7/2006 | Bonaventura et al. | |
| 7,087,769 B1 | 8/2006 | Contijoch Mestres et al. | |
| 2004/0122095 A1 | 6/2004 | Bonaventura et al. | |
| 2004/0166082 A1 | 8/2004 | Urgell-Beltran et al. | |
| 2004/0175350 A1 | 9/2004 | Urgell Beltran et al. | |
| 2004/0254232 A1 | 12/2004 | Beltran et al. | |
| 2004/0265443 A1 | 12/2004 | Beltran et al. | |
| 2005/0084471 A1 | 4/2005 | Andrews | |
| 2005/0175747 A1 | 8/2005 | Seguer Bonaventura et al. | |
| 2006/0024245 A1 * | 2/2006 | Gebreselassie et al. | 424/49 |
| 2006/0030512 A1 | 2/2006 | Hart | |
| 2009/0318557 A1 | 12/2009 | Stockel | |
| 2010/0056628 A1 | 3/2010 | Stockel et al. | |
| 2010/0173993 A1 | 7/2010 | Sawyer et al. | |

FOREIGN PATENT DOCUMENTS

| | | |
|---|---|---|
| EP | 2046316 B1 | 9/2010 |
| WO | WO 03/013454 A1 | 2/2003 |

* cited by examiner

*Primary Examiner* — Lezah Roberts
(74) *Attorney, Agent, or Firm* — Posz Law Group, PLC

(57) ABSTRACT

This invention pertains to dental care compositions with antimicrobial benefits. In particular, the invention provides for compositions of oral tissue-adherent salts that release biocidal ions on a controlled release basis and thereby provide and maintain an essentially uniform concentration of biocidal ions above the MBC or MIC of the target bacteria at the site of application in the mouth for an extended period of time. The compositions are useful for treating or preventing oral diseases resulting from bacteria, fungal or yeast infections, such as caries, gingivitis, periodontal disease and candidiasis.

6 Claims, No Drawings

COMPOSITIONS FOR DENTAL CARE

REFERENCE TO RELATED APPLICATIONS

This application is a continuation-in-part of application Ser. No. 11/599,758, filed Nov. 15, 2006 now abandoned (which is a continuation-in-part and claims the benefit of application Ser. No. 10/647,752, filed Aug. 26, 2003 now abandoned), the disclosure of which is incorporated herein in its entirety. This application claims the benefit of application Ser. No. 12/589,155, filed Oct. 19, 2009 (claiming the benefit of provisional application Ser. No. 61/196,455, filed Oct. 17, 2008) and also claims the benefit of application Ser. No. 11/633,231, filed Dec. 4, 2006 (claiming the benefit of provisional application Ser. No. 60/748,719 filed Dec. 9, 2005). Further, this application claims the benefit of application Ser. No. 10/770,248 filed Feb. 2, 2004 (claiming the benefit of provisional application Ser. No. 60/445,104 filed Feb. 6, 2003) now abandoned and also claims the benefit of application Ser. No. 10/972,567 filed Oct. 25, 2004 as a continuation-in-part of said application Ser. No. 10/770,248. Further, this application claims the benefit of application Ser. No. 12/798,479 filed Apr. 4, 2010, which is a continuation-in-part of application Ser. No. 12/586,695 filed Sep. 26, 2009 which is a continuation-in-part of application Ser. No. 11/517,147 filed Sep. 7, 2006, which claims the benefit of provisional application Ser. No. 60/719,900 filed Sep. 23, 2005. This application also claims the benefit of application Ser. No. 10/972,567 filed Oct. 25, 2004 as a continuation-in-part of said application Ser. No. 10/770,248 filed Feb. 2, 2004. The disclosures of all of the foregoing applications are incorporated by reference herein in their entirety.

FIELD OF THE INVENTION

This invention relates to oral care compositions and formulations which deliver and maintain uniform concentrations of antimicrobials to target areas in the mouth for an extended period of time.

BACKGROUND OF THE INVENTION

It is important to prevent the deterioration of oral health by maintaining good oral hygiene. However, there are many diseases which can occur in the mouth, apparently despite good oral hygiene practices. The diseases can seriously affect the health of oral tissue. Oral diseases not only result in the destruction of oral tissue but can also have systemic effects on the overall health of the human body. Therefore early effective treatment of oral infections is important.

Oral diseases are generally due to bacterial, fungal and yeast infections. For example dental caries is due to bacterial infections in the plaque biofilm on teeth. Cariogenic bacteria produce acids, which cause the development of demineralized subsurface lesions in mineralized tissue. These lesions grow in size eventually developing into cavities in the crowns and roots of teeth. If untreated, cavities can ultimately lead to the loss of teeth.

Gingivitis is also due to pathogenic bacteria in plaque biofilm. These bacteria produce toxins, which inflame the gingiva and cause the gums to bleeds. Many experts believe that gingivitis can lead to a more serious disease, periodontitis.

Periodontitis is also due bacterial infections. However, in this case the infection is below the gum line. In this disease the tissues around the roots of teeth become inflamed. The disease leads to loss of attachment and the formation of periodontal pockets. As the disease progresses there is loss of alveolar bone and eventually loss of teeth.

*Candida* infections, also known as thrush, are due to yeast infections and result in inflammation and the formation of potentially painful lesions in the oral mucosa.

Mechanical oral health measures alone while helpful may not be sufficient to maintain oral health. Often other medications are required to control oral diseases and prevent adverse effects. Since oral diseases are due to microbes, anti-microbial therapy can be important in the control of oral infections. However, due to their short residence time in the mouth topical application of antimicrobials to the mouth is usually relatively ineffective in eliminating the target bacteria.

OBJECTS OF THE INVENTION

It is an object of the invention to provide a safe and efficacious composition that will have a broad spectrum of activity against bacteria that are responsible for oral diseases and remain in the mouth at effective concentrations for extended periods of time.

It is a further object of the invention to provide a safe and efficacious composition that is adherent to oral tissues and releases and thereafter continuously maintains uniform concentrations of antimicrobial agents in the area being treated.

It is also an additional object of the invention to provide formulations and delivery vehicles that allow biocidal and biostatic compositions of the invention to be conveniently applied to various regions of the mouth where needed.

DETAILED DESCRIPTION OF THE INVENTION

The foregoing objects of the invention and additional objects are met by providing oral treatment compositions which are adherent to oral tissues and which release even concentrations of one or more biocidal or biostatic components for extended periods.

Essentially the invention provides for an oral treatment composition containing a controlled release, oral tissue-adherent salt, comprising anionic and cationic components, either or both of which have significant biocidal or biostatic activity, whereby said salt has (i) an aqueous solubility enabling it to release dissolved biocidal or biostatic cations or biocidal or biostatic anions into the oral fluid at a concentration that is equal to or exceeds the MBC or MIC of the target bacteria, while (ii) the aqueous solubility of said salt is appropriately limited to leave undissolved, un-dissociated salt on the oral tissues to which it was applied, to allow the subsequent release of additional biocidal or biostatic ions into the mouth and thereby replace the dissolved biocidal or biostatic ions that are used up or otherwise depleted, thereby maintaining an essentially uniform concentration of biocidal or biostatic ions equal to or exceeding the MBC or MIC of the target bacteria in the oral fluid for an extended period of time.

As noted, the controlled release, oral tissue-adherent salts employed comprise cationic and anionic components, one or other or both of which are biocidal or biostatic to the target bacteria. The controlled release properties of the salt are primarily influenced by the solubility of the oral tissue-adherent salt. Thus, the salt needs to be sufficiently soluble to release enough biocidal component to exceed the minimum bactericidal concentration (MBC) or minimum inhibitory concentration (MIC) of that component to the target bacteria. However, the solubility of the salt should be such that much of the applied oral tissue-adherent salt remains in undissolved form to release additional biocidal component to replace that used up or depleted from the target area.

Typically, the biocidal or biostatic cationic or anionic components of the invention have MBCs in the range from about 0.1 ppm to about 1000 ppm against a broad range of bacteria. Hence in order to be effective the solubility of the tissue-adherent salt ideally needs to be at least about 5 ppm and up to about 2000 ppm depending on the susceptibility of the target bacteria to the biocidal ions. On the other hand, the solubility of the salt should generally be no more than from about 200 ppm (0.02%) to no more than about 10,000 ppm, (1%) to insure that a reservoir of undissolved tissue-adherent salt remains at the site where it is applied for an extended period of time.

The oral treatment composition comprises cationic and anionic components at least one of which is biocidal or biostatic. Biocidal cationic components of the invention preferably have primary ammonium, secondary ammonium, tertiary ammonium, quaternary ammonium, guanidino, or biguanidino functionality. Examples of highly effective biocidal cations include but are not limited to ($C_8$-$C_{18}$) alkyl dimethyl benzyl ammonium ions, ($C_8$-$C_{18}$) alkyl trimethyl ammonium ions, ($C_8$-$C_{18}$) dialkyl methyl benzyl ammonium ions, ($C_8$-$C_{18}$) dialkyl dimethyl ammonium ions, benzalkonium ions, benzethonium ions, sanguinarium ions, cetylpyridinium ions, hexetidinium ions, alexidinium ions, chlorhexidinium ions, octenidinium ions, polyhexamethylene biguanidino (PHMB) ions, polyhexamethylene guanidino ions, and polyquaternium-2 ions.

In the preparation of oral tissue adherent salts, it is especially desirable to utilize components which are derived from natural renewable sources of ingredients. Compounds based on renewable-sourced ingredients are generally safer to humans, being completely metabolized by the body to non-toxic compounds, like carbon dioxide and water. Many of these compounds are less cyto-toxic and hence are less irritating to the skin, mucosa and eyes. Additionally such compounds are also more fully biodegraded in the environment and do not leave environmentally undesirable residues.

Examples of such naturally derived cations include biocidal or biostatic cations of (i) a $C_8$-$C_{18}$ alkyl ester of an mono-carboxylic amino acid, of a peptide, of carnitine, of creatine and of glycine betaine, (ii) a $C_2$-$C_{18}$ dialkyl ester of a dicarboxylic amino acid (iii) a $C_2$-$C_{18}$ alkyl ester of a $C_8$-$C_{18}$ acyl ester of serine, threonine and carnitine, (iv) a $C_8$-$C_{18}$ acyl ester of choline and (v) a $C_1$-$C_{18}$ alkyl ester of a $C_2$-$C_{18}$ mono-acyl amide of a dibasic amino acid or a polybasic peptide.

Of course, these compounds and be prepared form synthetic sources and would retain many of the environmental and safety benefits of their naturally derived analogues.

Another group of useful cationic component for the controlled release, oral tissue-adherent salts are antibiotics with cationic functionality. Examples include tetracycline, aureomycin, terramycin, tigecycline, doxycycline, minocycline, demeclocycline, lymecycline, meclocycline, methacycline, rolitetracycline, and clindamycin.

When the anionic component of the controlled release, oral tissue-adherent salt is biocidal or biostatic, a cationic component may be chosen which is biocidally inactive. In this case, the cationic counter ion is selected on the basis of the solubility of the resulting salt and how well the salt adheres to oral tissue. Examples or inactive cations for this use include polyamine, polyethyleneimine and polyammonium ions, various polymers and copolymers with quaternary ammonium groupings including polyquaternium-4 (Celquat®), polyquaternium-10, polyquaternium-11, polyquaternium-22, polyquaternium-28, polyquaternium-32 and polyquaternium-37.

Useful biocidal or biostatic anionic components for the controlled release tissue adherent salt include anions with phenolic functionality Examples of these anions are phenolate, resorcinolate, parachlorophenolate, trichlorophenolate (TCP anion), o-phenylphenolate, the phenolate anion of trichloro-hydroxy-diphenyl ether (triclosan anion), phenolate anions of parachloro-metaxylenol (PCMX anion), phenolate ions of thymol, 4-allyl-2-methoxy phenolate (eugenol anions), hexachlorophenate anions and various polyphenolate anions.

Another group of useful biocidal anions include antibiotics with anionic functionality. These include the anions of penicillin and its derivatives.

When the cationic component of the controlled release tissue adherent salt has biocidal of biostatic activity, the anionic component maybe inactive. In this case the anion is selected on the basis of the solubility of the resulting salt and its contribution to the ability of the salt to stick to oral tissue surfaces. Examples of such suitable anions include those with mono- or polycarboxylate functionality. These include the anions of a $C_8$-$C_{18}$ monocarboxylic acid. It has been found that the solubility and oral tissue adherence of the resulting controlled release oral tissue-adherent salt decreases with increasing number of carbon atoms in the carboxylic acid. Another group of useful anions include the anions of polycarboxylic acid such as malic acid, maleic acid, fumaric acid, tartaric acid, succinic acid, adipic acid, malonic acid, citric acid, polyacrylic acid, alginic acid, xanthan, polysaccharide and vinyl ether/maleic acid copolymer.

One preferred group of controlled release, oral tissue-adherent salts are the salts of a $C_8$-$C_{18}$ carboxylic acid with a $N^\alpha$-($C_8$-$C_{18}$) acyl ($C_2$-$C_{18}$) alkyl ester of a dibasic amino acid selected from the group arginine, lysine, ornithine and histidine. A particularly preferred member of this group is the laurate salt of $N^\alpha$-lauroyl ethyl ester of arginine.

The controlled release, oral tissue adherent salts can be prepared by any means. A particularly simple method is by the metathesis reaction of two soluble salts to form the desired less soluble target controlled release, skin adherent salt. Another straightforward method of preparing the salts is by the direct reaction of the anionic acid with the cationic base. The salts can be preformed before incorporating them into compositions of the invention. Alternatively the salts can be formed by application of two separate salt solution components, one component containing the cation and one component containing the anion, to the target area to form the salt in situ, by physically segregating the two components prior to use, then separately or simultaneously adding the two components to the target area to form the salt. For example, as a treatment for periodontitis, the salt can be formed by metathesis directly within the gingival pocket by simultaneously application of solutions of soluble salts each of which contains the two ionic portions of the medicinal salt, so that it precipitates in situ and adheres to the sub-gingival tissue. Therefore one component containing the cation and one component containing the anion can be formed in situ where needed at the oral-tissue treatment target area by application of separate salts of the anionic acid and cationic base.

The controlled release oral tissue-adherent salts may attach themselves more effectively to mineralized tissue or to soft oral tissue. For example, supra-gingival treatment salts may become strongly attached to tooth enamel surfaces or to the gingival or other mucosal surfaces. Sub-gingival treatment salts may most effectively be attached to the dentin or to areas of sub-gingival soft tissue.

Oral treatment compositions of the invention are useful for treating and prevent any kind of bacterial, fungal or yeast based infections of the mouth. Thus, when applied supragingivally, the compositions of the invention can kill disease bacteria such as *s. mutans, s. sobrinus* and lactobacilli which are responsible for dental caries. Removal of cariogenic bacteria protects the teeth against the formation of decalcified lesions and cavities. The compositions are also effective in controlling bacteria responsible for gingivitis and bleeding gums. Suitable controlled release, tissue adherent salts are effective against fungal infections and yeasts which cause candidiasis. When applied below the gumline compositions of the invention are effective in controlling the anaerobic bacteria responsible for periodontal diseases.

The compositions of the invention can be applied to the teeth and gums in different forms. Toothpastes, gels, trays, mouthwashes and irrigating devices are suitable for applying the compositions to teeth and gums. Dental floss with these salts can be used to ensure that the treatments get between teeth. Denture appliances can be treated with compositions of the invention to treat or prevent candidiasis. Compositions of the invention can also be applied using a sub-gingival syringe for the treatment of periodontal disease.

Since the controlled release, oral tissue-adherent salts tend to have low aqueous solubility, when incorporated into formulations such as toothpastes, gels and mouthwashes these salts are either dispersed as fine particles into the formulation or dispersed as micro-emulsions.

This invention thus also provides for a method of treating oral diseases in the mouth, by the application to the target area of the mouth of an oral treatment composition containing (1) a controlled release, oral tissue-adherent salt comprising anionic and cationic components, either or both of which have significant biocidal or biostatic activity, whereby said salt has (i) an aqueous solubility enabling it to release dissolved biocidal or biostatic anions or biocidal or biostatic cations into the oral fluid at a concentration that is equal to or exceeds the MBC or MIC of the target bacteria, while (ii) the aqueous solubility of said salt is appropriately limited to leave undissolved, un-dissociated salt on the oral tissues to which it was applied, to act as a reservoir to allow the subsequent release of additional biocidal or biostatic ions into the mouth, to replace the dissolved biocidal or biostatic ions as they are used up or otherwise depleted, thereby maintaining an essentially uniform concentration of biocidal or biostatic ions equal to or exceeding the MBC or MIC of the target bacteria in the oral fluid in the treated area of the mouth for an extended period of time.

EXAMPLES

The following non-limiting examples serve to illustrate the various embodiments of this invention.

Example I

Dental Floss to Treat Gingivitis

To a 5 g sample of a chlorhexidine-triclosan complex was added 60 g of PEG 3350, 30 g PEG 1000 and 5 g glycerin. The mixture was gently heated and stirred to dissolve the complex. The resultant warm solution was used to coat a commercial non-wax dental floss to provide an efficacious germicidal dental floss. The floss is used to treat gingivitis. When teeth are flossed the controlled release salt is deposited between teeth. A synergistic combination of chlorhexidine cations and triclosan anions is gradually released reducing the interproximal plaque and reducing the tendency for bleeding gums.

Example II

Periodontal Composition to Treat Periodontitis $N^\alpha$-lauroyl arginine ethyl ester laurate salt (40 g) is melted with glycerin (60 g) at about 60° C. and mixed until a thick paste is formed. The paste is allowed to cool to room temperature. The paste is used to treat periodontitius by applying 150 to 300 mg this paste into the periodontal pocket. After 2 days the overall count of anaerobic bacteria measurably reduced. After three weeks inflammation is reduced and there appear to be initial signs of gum reattachment. Three months later pocket depth is reduced by 2 mm and no inflammation is apparent.

Example III

Antimicrobial Treatment for the Prevention of Caries and Gingivitis in High Risk Populations The following formulation is prepared

| Part I | |
|---|---|
| Cetyl pyridinium chloride | 1.0 |
| Water | 50.0 |
| Part 2 | |
| Carbomer 941 | 0.5 |
| Water | 48.5 |
| Triethanolamine | To pH 5.5 |

Cetyl pyridinium chloride is dissolved in cold deionized water. A separate dispersion of Carbomer 941 is prepared in deionized water at 60° C. The cetyl pyridinium solution is added with stirring to the Carbomer solution. Finally the pH of the mixture is adjusted to between 4.5 and 6.0 using triethanolamine. Cetyl pyridinium-carbomer salt controlled release, oral tissue adhesive salt is formed in situ. The gel is topically applied to teeth and gums using a swab to reduce bacterial counts of bacteria causing dental caries and gingivitis.

Example IV

Prevention and Treatment of Candidiasis

An orally acceptable cream containing 0.5% dodecyl dimethyl ammonium thymolate is applied to the surfaces of dentures and other oral appliances to eradicate candida infections thereon. The cream can also be applied to the oral pallet, tongue and oral mucosa. It is preferable to leave the cream in place for at least an hour before eating, drinking or brushing teeth.

Table 1—Comparison of Several LAE Salts Against Two Common Oral Bacteria Using a Zone of Inhibition Test.

In Table 1, Agar plates were seeded with either *S. mutans* or *S. pyogenes* and $N^\alpha$-lauroyl arginine ethyl ester salts ("LAE salts") were applied. After 3 days, the plates were examined for bacterial growth and the presence of a zone of inhibition around the applied salt. For *S. pyogenes*, a reduction of zone of inhibition size was seen with increasing size of the anion from acetate to laurate, showing decreased bio-availability and increased retention in the salt form. *S. mutans* shows no such dependency, suggesting that maximal inhibition was achieved by the material released from the laurate salt.

In Table 1, LAE-HCl was reacted with a series of fatty acids of increasing molecular weight, which is proportional to antimicrobial retention, but inversely-proportional to the bioavailability of the free antimicrobial ion. In another words, a pairing was developed, which would be soluble enough to release the antimicrobial agent into the periodontal pocket at a concentration which kills or inhibits the growth of periodontal bacteria, but sufficiently limited to act as a reservoir for the release of additional antimicrobial agent as the dissolved one gets used up or is flushed from the area.

TABLE 1

Comparison of LAE salts against two common oral bacteria

| Sample # | Compound | Zone of Inhibition (mm) | |
|---|---|---|---|
| | | S. mutans | S. pyogenes |
| 1 | LAE-hydrochloride salt | 8 | 5 |
| 2 | LAE acetate | 8 | 10 |
| 3 | LAE lactate | 7 | 6 |
| 4 | LAE octanoate | 5 | 3 |
| 5 | LAE laurate | 8 | 2 |

In order to determine whether the adhesive laurate ion would interfere with the attachment and biological functions of cells, an experiment was performed, in which the bottom of a cell culture plate was coated with lauric acid and plated cells on top of it. Microphotographs showed normal morphology cells homing in the laurate-covered areas −24 h after plating. Normally proliferating cells were observed 11 days later beneath the laurate matrix (scraped for clarity), indicating that at least in this model system, the presence of lauric ion coating does not seem to be a physical impediment to the periodontal regeneration.

Prototypes of $N^\alpha$-lauroyl arginine ethyl ester (LAE) salt and of a minocycline salt of lauric acid would carry an added value of regenerative potential through inhibition of inflammation-associated proteases, and through the release of arginine—a well-known mediator of tissue repair—in the case of LAE (Poiarkov et al., 2007, Debats et al., 2009).

The invention claimed is:

1. A method of treating oral diseases in the mouth, said method comprising the step of applying to the target area of the mouth an oral treatment composition comprising a controlled release, oral tissue-adherent salt comprising C8-C18 monocarboxylic acid anionic and $N^\alpha$-(C8-C18)acyl(C2-C18) alkyl ester of a dibasic amino acid cationic components, whereby said salt has (i) an aqueous solubility from about 200 ppm to about 10,000 ppm enabling it to release dissolved biocidal or biostatic cations into the oral fluid at a concentration that is equal to or exceeds the minimum bactericidal concentration (MBC) or minimum inhibitory concentration (MIC) of the target bacteria, while (ii) the aqueous solubility of said salt is appropriately limited to leave undissolved, un-dissociated salt on the oral tissues to which it was applied, to act as a reservoir to allow the subsequent release of additional biocidal or biostatic ions into the mouth, to replace the dissolved biocidal or biostatic ions as they are used up or otherwise depleted, thereby maintaining an essentially uniform concentration of biocidal or biostatic ions equal to or exceeding the MBC or MIC of the target bacteria in the oral fluid in the treated area of the mouth for an extended period of time.

2. The method of treating oral diseases of claim 1, in which the oral treatment composition is applied to the soft or mineralized oral tissue above the gum line as a supra-gingival treatment to control bacteria, fungi and yeasts in the prevention and treatment of dental caries, gingivitis, candidiasis or other oral diseases.

3. The method of treating oral diseases of claim 1, in which the oral treatment composition is applied to the soft or mineralized oral tissue below the gum line as a sub-gingival treatment to control periodontal pathogens and treat periodontal disease.

4. The method of treating oral diseases of claim 1, in which the controlled release, oral tissue-adherent salt is preformed or is formed by application of two separate salt solution components, one component containing the cation and one component containing the anion, to the target area by physically segregating the two components prior to use, then separately or simultaneously adding the two components to the target area to form the salt in situ.

5. The method of treating oral diseases of claim 1, in which the controlled release, oral tissue-adherent salt is delivered to the teeth, gums, gingival pockets or other area of the mouth in a toothpaste, a tooth gel, a mouthwash, dental floss, a sub-gingival syringe, a tray, a treatment strip, an ointment, a dental appliance, a denture appliance or other type device for delivery of the oral tissue-adherent salt.

6. The method of treating oral diseases of claim 1, in which the C8-C18 monocarboxylic acid anionic component is octanoic acid and the $N\alpha$-(C8-C18) acyl (C2-C18) alkyl ester of a dibasic amino acid cationic component is $N\alpha$-(C8-C18) acyl (C2-C18) alkyl ester of arginine.

* * * * *